United States Patent [19]
Shroot et al.

[11] Patent Number: 5,151,534
[45] Date of Patent: Sep. 29, 1992

[54] SULPHUR-CONTAINING EICOSANOIDES AND THEIR APPLICATION IN PHARMACY AND IN COSMETICS

[75] Inventors: Braham Shroot, Antibes; Christopher Hensby, Biot; Jean Maignan, Tremblay les Gonesse; Gerard Lang, Saint Gratien; Michel Colin, Livry Gargan, all of France

[73] Assignee: Centre International De Recherches Dermatologiques (CIRD), Valbonne, France

[21] Appl. No.: 349,691

[22] Filed: May 10, 1989

[30] Foreign Application Priority Data

May 10, 1988 [FR] France .................. 8806313

[51] Int. Cl.$^5$ .............................. C08H 3/00
[52] U.S. Cl. ..................... 554/88; 554/101; 514/886; 514/887
[58] Field of Search ............ 260/404, 413 L, 399, 260/400, 413; 514/558, 886, 887

[56] References Cited

U.S. PATENT DOCUMENTS 3,033,884  5/1962  Osbond et al. ............. 260/413

OTHER PUBLICATIONS

Guindon et al., J. Organic Chemistry, vol. 53, 1988 pp. 267–275.
Chemical Abstracts, vol. 108, #7, p. 686, 1988 55689k, abs of Guindon et al article.

Primary Examiner—Jose G. Dees
Assistant Examiner—D. P. Carr
Attorney, Agent, or Firm—Cushman, Darby & Cushman

[57] ABSTRACT

Compounds corresponding to the formula:

$$C_5H_{11}-A-CH_2-C\equiv C-CH_2-C\equiv C-$$
$$-CH_2-C\equiv C-CH_2-\underset{\underset{(O)_n}{\downarrow}}{S}-CH_2-COR$$

wherein
A represents $-(CH_2)_2-$ or $-(C\equiv C)-$;
n is equal to 0, 1 or 2;
R represents hydroxyl, alkoxy having the formula $-OR_1$, or amino having the formula $$-N\begin{matrix}R_2\\R_3\end{matrix}$$

$R_1$ represents alkyl, monohydroxyalkyl, polyhydroxyalkyl, aryl or aralkyl;
$R_2$ and $R_3$ represent hydrogen, alkyl, monohydroxyalkyl, polyhydroxyalkyl, aryl or benzyl;
$R_2$ and $R_3$ form, with the nitrogen atom, a heterocyclic ring.

Application of these compounds in pharmacy and cosmetics.

12 Claims, No Drawings

SULPHUR-CONTAINING EICOSANOIDES AND THEIR APPLICATION IN PHARMACY AND IN COSMETICS

The present invention relates to new derivatives of 5,8,11-eicosatriynoic and 5,8,11,14-eicosatetraynoic acids and to their use as therapeutic agents in the treatment or the prophylaxis of allergic diseases, in the treatment of dermatitis, and in the treatment of inflammatory diseases and in cosmetic compositions.

It is known that a certain number of substances play an important part in the inflammatory process of the skin, such as acne, dermatitis such as, for example, psoriasis, eczema, and the like. These substances, which include the prostaglandins, hydroxyeicosatetraynoic acids, thromboxanes and leucotrienes, all have a common source, which is arachidonic acid (see, in particular, Voorhees "Leukotrienes and Other Lipoxygenase Products in the Pathogenesis and Therapy of Psoriasis and Other Dermatoses", Arch. Dermatol., Vol. 119, July 1983, 541–547).

The formation of these substances is essentially the result of conversion of the arachidonic acid linked by an ester bond to the lipids present in the epidermis (for example the phospholipids), after it has been released.

Cyclooxygenase inhibitors, which prevent the formation of prostaglandins such as indomethacin, vitamin E and the like, or else substances capable of inhibiting the lipoxygenases, such as eicosatetraynoic acid, have already been recommended previously for the treatment of skin disorders.

5,8,11,14-eicosatetraynoic acid, as well as 5,8,11-eicosatriynoic acid and their lower alkyl esters have also been proposed for the treatment of psoriasis, especially in U.S. Pat. No. 4,190,669.

The applicants have found that, surprisingly, products which inhibit the enzyme metabolism of arachidonic acid, induced by cyclooxygenase, and the lipoxygenases, are obtained when the methylene group in position 3 in the structure of 5,8,11-eicosatriynoic acid or of 5,8,11,14-eicosatetraynoic acid is replaced with a heteroatom, such as sulphur, or with a sulphoxide or sulphone group.

These acids, which have a thioether functional group in position 3, offer the additional advantage of being much more advantageous in the cost of manufacture, since the last two stages of synthesis involve propargyl alcohol and thioglycolic acid, which are two readily available raw materials.

Surprisingly, these thioether, sulphoxide or sulphone compounds exhibit a bioavailability which is different from that of the corresponding 5,8,11-eicosatriynoic or 5,8,11,14-eicosatetraynoic acids.

In fact, with this new sulphoxide and, above all, sulphone functional group, it is possible to obtain products of very different polarity. For example, when it is a sulphone functional group, the corresponding 3,3-dioxo-3-thia-5,8,11-eicosatriynoic and 3,3-dioxo-3-thia-5,8,11,14-eicosatetraynoic acids, converted into salts with a tertiary amine such as triethanolamine, are soluble in water in a concentration of more than 10%, whereas the solubility of salts of the acids whose chain consists entirely of carbons is lower than 1%.

It is known, furthermore, that the lower alkyl esters of both these carbon-containing acids are unstable and decompose during their purification, whereas, for example, methyl 3,3-dioxo-3-thia-5,8,11-eicosatriynoate is isolated without difficulty.

The present invention therefore relates to these new acids, as well as to their derivatives, such as esters and amides.

The present invention also relates to a process for the preparation of these derivatives.

The present invention further relates to pharmaceutical compositions containing these compounds as an active substance.

Finally, the present invention relates to the use, in the cosmetic field, of these compounds and the corresponding cosmetic compositions, especially in antiacne, antisunburn or postsunbathing compositions, or in the treatment of seborrhoeic dermatitis.

Other objects of the present invention appear in the description and the examples which follow.

The compounds in accordance with the present invention are essentially characterized in that they correspond to the general formula (I):

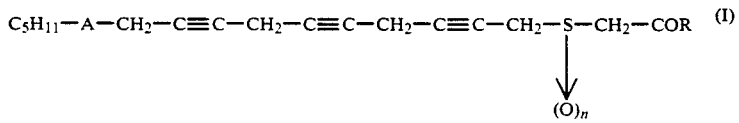

wherein
A represents $-(CH_2)_2$ or $-C \equiv C-$;
n is equal to 0, 1 or 2;
R represents hydroxyl, alkoxy having the formula $-OR_1$, or amino having the formula:

wherein
$R_1$ represents alkyl containing from 1 to 20 carbon atoms, monohydroxyalkyl, polyhydroxyalkyl, aryl or aralkyl radical, optionally substituted, or a sugar residue;
$R_2$ and $R_3$, each independently, represent hydrogen, lower alkyl, monohydroxyalkyl optionally interrupted by a heteroatom, polyhydroxyalkyl, aryl or benzyl, optionally substituted, an amino acid residue or an amino sugar residue;
$R_2$ and $R_3$, together with the nitrogen atom to which they are attached can also form a heterocyclic ring, optionally containing an additional heteroatom and/or optionally substituted by alkyl or hydroxyalkyl,
and to their salts and their optical and geometric isomers.

By lower alkyl is meant alkyl containing 1 to 6 carbon atoms.

Representative alkyl radicals containing up to 20 carbon atoms include methyl, ethyl, isopropyl, butyl, tert-butyl, 2-ethylhexyl, isooctyl, dodecyl, hexadecyl and octadecyl radicals.

By monohydroxyalkyl, optionally interrupted by a heteroatom, is meant a radical containing 2 to 6 carbon atoms, optionally interrupted by an oxygen atom, and more particularly a 2-hydroxyethyl, 2-hydroxypropyl or 2-hydroxyethoxyethyl radical.

By polyhydroxyalkyl is meant, preferably, a radical containing from 3 to 6 carbon atoms and from 2 to 5 hydroxyl groups, such as 2,3-dihydroxypropyl, 1,3-dihydroxy-2-propyl, or pentaerythritol residue.

By aryl is meant phenyl, optionally substituted by at least one halogen, —OH, —NO$_2$, lower alkyl, trifluoromethyl or a carboxylic acid functional group.

The preferred aralkyl radicals are benzyl or phenethyl radicals.

By sugar residue is meant, preferably, a radical derived from glucose, mannose, erythrose or galactose.

Representative sugar residues include, particularly, those derived from glucosamine, galactosamine, mannosamine or meglumine.

When the radicals R$_2$ and R$_3$, taken together, form a heterocyclic ring with the nitrogen atom to which they are attached, this ring is preferably a piperidino, piperazino, morpholino, pyrrolidino or 4-(2-hydroxyethyl)-piperazino radical.

The salts of the compounds in accordance with the present invention are chosen particularly from alkali or alkaline-earth metal salts, or else from zinc or organic amine salts, or quaternary ammonium salts, when they contain at least one free acidic functional group; or the salts of an inorganic or organic acid, especially hydrochlorides, hydrobromides or citrates, when they contain at least one amine functional group.

The acids which are particularly preferred, in accordance with the present invention, are the following:
  3-thia-5,8,11-eicosatriynoic;
  3-thia-5,8,11,14-eicosatetraynoic;
  3,3-dioxo-3-thia-5,8,11,14-eicosatriynoic;
  3,3-dioxo-3-thia-5,8,11,14-eicosatetraynoic; and their amides.

The compounds in accordance with the present invention can be prepared by using the following procedures:

3-thia-5,8,11-eicosatriynoic acid is prepared according to reaction scheme A from 1-decyne (1). The anion of the latter, formed by reaction with a strong base, such as an alkylmagnesium halide, is reacted with an excess of 1,4-dihalo-2-butyne and leads to 1-halo-2,5-tetradecadiyne (2), the preparation of which is described in French Patent 2,584,400.

This halide (2) is reacted with the dianion of propargyl alcohol, formed by treating this alcohol with 2 base equivalents. The bases employed are strong bases, such as organolithium compounds such as, for example, butyllithium, or organomagnesium compounds such as ethyl- or propylmagnesium halide in an anhydrous solvent, preferably an ether such as tetrahydrofuran or diethyl ether.

After acidification of the reaction mixture, 2,5,8-heptadecatriyn-1-ol (3) is obtained, and is purified by recrystallization.

In a third stage, this alcohol (3) is treated in a chlorinated solvent, such as dichloromethane or 1,2-dichloroethane or an ether, with a phosphorus trihalide.

The 1-halo-2,5,8-heptadecatriyne (4) is then reacted directly with the dianion of thioglycolic acid, HS—CH$_2$—CO$_2$H, formed by treating the latter with 2 equivalents of an inorganic or organic base.

The preferred bases are sodium hydroxide, potassium hydroxide or sodium methanolate.

3-thia-5,8,11-eicosatriynoic acid (5) is purified by crystallization from a suitable solvent.

REACTION SCHEME A

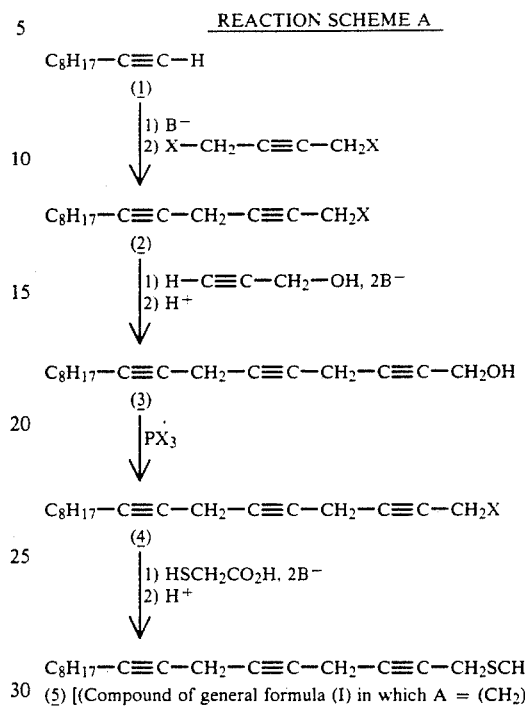

The tetraynoic acids are synthesized by following the same principle, using reaction scheme B and starting with 1-heptyne (6).

The anion of the latter, treated with 1,4-dihalobutyne, leads to 1-halo-2,5-undecadiyne (7). This synthesis is described more particularly in French Patent Application No. 86/18,419.

The conversion of the halide containing 11 carbon atoms of formula (7) to 1-hydroxy-2,5,8-tetradecatriyne (8) is obtained by the action of the dianion of propargyl alcohol. This alcohol of formula (3) is, in turn, converted into 1-halo-2,5,8-tetradecatriyne of formula (9) by the action of a phosphorus trihalide.

By following experimental conditions identical with the two preceding stages, the halide (9) is converted by the action of the dianion of propargyl alcohol into 2,5,8,11-heptadecatetrayn-1-ol (10). The latter is converted to 1-halo-2,5,8,11-heptadecatetrayne (11) by the action of phosphorus trihalide.

The synthesis of 1-bromo-2,5,8,11-heptadecatetrayne is described in U.S. Pat. No. 3,033,884.

As in the case of reaction scheme A, the 1-halo-2,5,8,11-heptadecatetrayne (11) is then reacted directly with the dianion of the acid H—S—CH$_2$CO$_2$H formed by treating the latter with 2 equivalents of a base.

REACTION SCHEME B

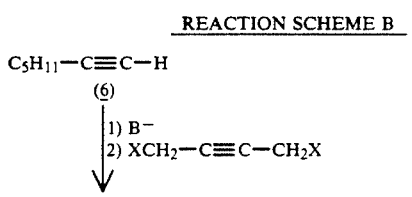

-continued
REACTION SCHEME B

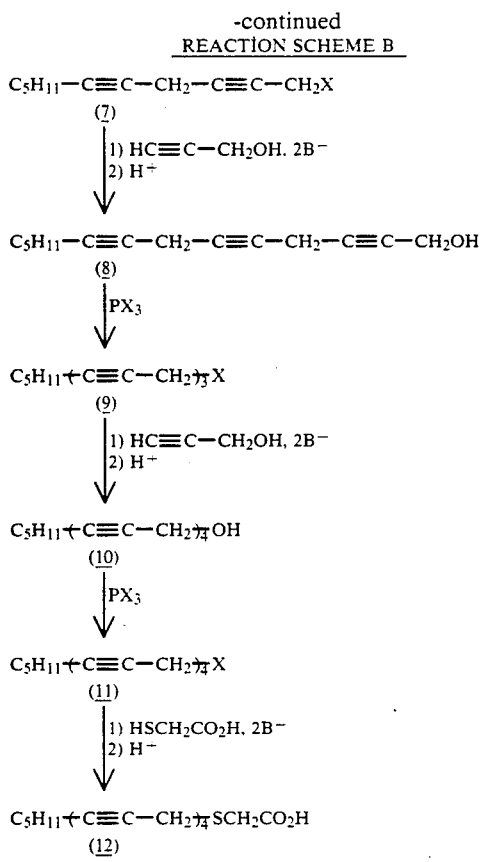

The acids of general formula (I') can be converted into the corresponding esters (II) by following the usual methods for converting an acid into an ester, that is to say, by the action of an alcohol in an acidic medium or by reaction of displacing the halogen of an alkyl halide by the sodium or potassium carboxylate functional group of the acid (I').

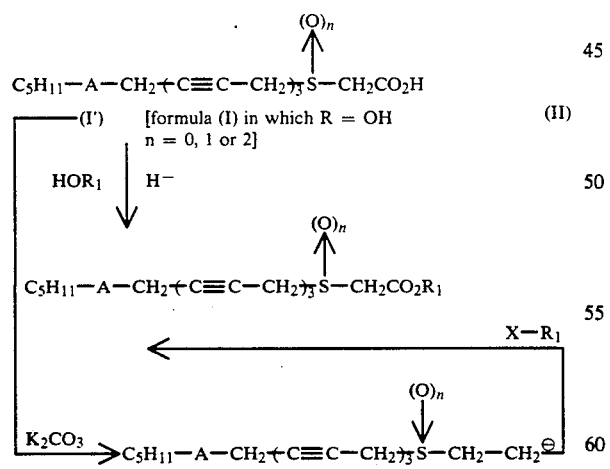

In the abovementioned formula, $R_1$ has the meanings shown above and X represents halogen such as chlorine or bromine.

The amides of general formula (III) falling within the definition o the general formula (I) in which R denotes the group:

in accordance with the present invention, are obtained by reacting an activated form of the acid of formula (I') with an amine in an organic solvent. This activated form of the acid can be either an acid chloride or an anhydride or else the intermediate formed by the addition of carbonyldiimidazole (CDI) to a solution of the acid.

This latter reaction is preferably conducted in a solvent medium such as dimethylformamide or a chlorinated solvent, such as dichloromethane or 1,2-dichloroethane. This reaction takes place, in particular, according to the following reaction scheme:

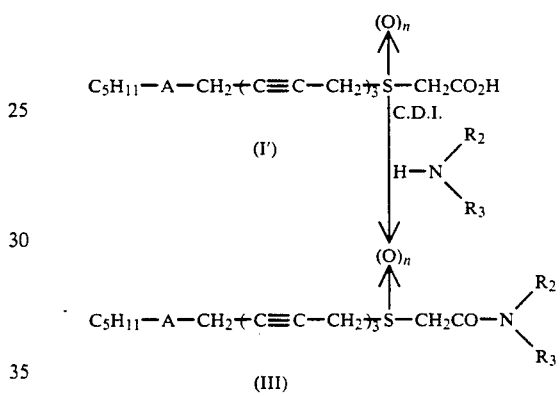

When the thioglycolamides are easily accessible, the amides of structure (III) can be obtained directly without proceeding through the acid of formula (I') (reaction scheme C), by treating the halide (4) or (11) with the thiolate formed from the thioglycolamide (13). The latter is prepared by the action of an amine

with ethyl thioglycolate (14). In fact, this method is simpler. The halides (4) or (11), on the one hand, and the sodium or potassium salt of thioglycolamide, on the other hand, are prepared in methanol or ethanol. The halides (4) or (11) are not purified and their reaction mixture is added directly to an alcoholic solution of the ethioglycolamide converted into salt form with one equivalent of a base.

REACTION SCHEME C

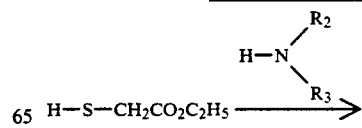

-continued
REACTION SCHEME C

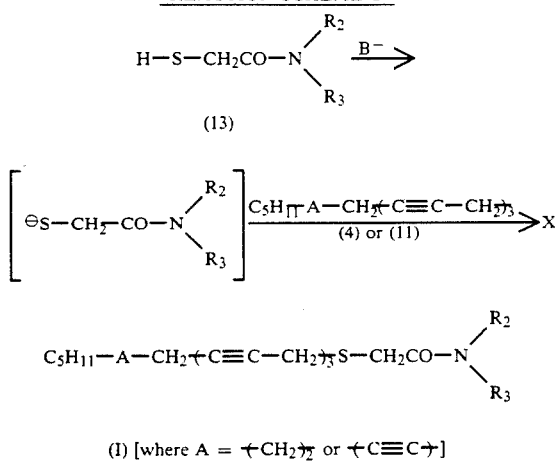

(I) [where A = $+CH_2+_2$ or $+C\equiv C+$]

The sulphoxides or the sulphones of general formula (I) (n=1 or 2) are prepared from the corresponding thioethers by the action of one equivalent or two equivalents of an organic peracid (15) in an organic solvent, such as methylene chloride or 1,2-dichloroethane. (Reaction scheme D)

REACTION SCHEME D

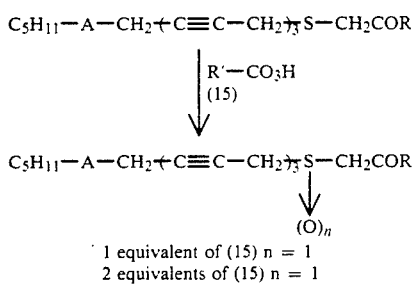

1 equivalent of (15) n = 1
2 equivalents of (15) n = 1

The sulphoxides falling within the definition of the general formula (I) can also be synthesized by oxidation of the corresponding thioether, using sodium bromite.

The compounds of formula (I), in accordance with the present invention, have a particularly remarkable activity towards the inhibition of the metabolism of arachidonic acid and especially with regard to the lipoxygenases at the origin of the formation of the leucotrienes and of the hydroxylated acids which play an important part in the inflammatory process.

They can be administered to man or animal with the aid of compositions which additionally contain a pharmaceutically acceptable carrier or diluent. If desired, these compounds can also be used in combination with other active substances which have no antagonist effect.

The pharmaceutical or veterinary compositions in accordance with the present invention can be administered by a systemic or local route.

In the case of enteral administration, they can be provided in the form of tablets, gelatin capsules, pills, suppositories, syrups, suspensions, solutions, powders, granules, emulsions, and the like.

In the case of topical administration, the pharmaceutical compositions can be provided, inter alia, in the form of ointments, tinctures, creams, pomades, powders, patches, saturated pads, solutions, lotions, gels, sprays, shampoos or suspensions, or in the form of microdispersions of ionic or nonionic lipidic microcapsules, optionally containing an oil.

The compositions for topical administration can be provided either in anhydrous or aqueous form, depending on the clinical indication.

In the case of ophthalmic administration, a sterile aqueous eye lotion can be employed in the form of a suspension wherein the active substance has a particle size smaller than 25 μm, according to pharmacopoeia indications. It is also possible to employ an ophthalmic pomade in which the active substance is dissolved. This pomade comprises a suitable mixture of polyethylene glycol and the active substance.

The present invention also related to sprayable compositions such as mouth and throat sprays comprising a hydroethanolic solution or a suspension of the active substance in a dispersed phase and having a suitable particle size.

The pharmaceutical compositions, in accordance with the present invention can also be administered parenterally and especially intravenously, intramuscularly, intraperitoneally, subcutaneously or intradermally.

In the case of the parenteral administration, and more particularly by injection, the active substance is employed in a sterile carrier such as water. The active substance is either suspended or dissolved in this carrier or in an ionic or nonionic lipidic microcapsule.

In the case of the intramuscular or subcutaneous administration, the active substance can be provided in the form:

of a suspension or dispersion in an aqueous solution, for example a solution of benzyl alcohol, sodium carboxymethyl cellulose, sodium chloride, the condensation product of 20 moles of ethylene oxide with a mixture of sorbitol oleic esters and of sorbitol anhydrides called "Polysorbate 80", and water for use as an injectable preparation;

of a solution in a nonaqueous solvent comprising a vegetable oil, e.g. castor oil, for injectable preparations, to which a low percentage of ethyl alcohol has or has not been added. The sterilization of the nonaqueous solution can be performed by filtration.

The compounds in accordance with the present invention can also be employed in cosmetics, especially in creams, in skin lotions such as in antisunburn, post sunbathing, soothing, and antiseborrhoeic lotions and in antiacne products or in shampoos.

The pharmaceutical and/or cosmetic compositions in accordance with the invention can contain inert or pharmacodynamically or cosmetically active additives, and especially:

hydrating agents such as thiamorpholinone and its derivatives or urea; antiseborrhoeic agents such as S-carboxymethylcysteine, S-benzylcysteamine and their derivatives, thioxolone; antibiotics such as erythromycin and its esters, neomycin, clindamycin and its derivatives, or tetracyclines; agents which interfere with keratinization, such as salicylic acid and α-hydroxycarboxylic acids; agents promoting fresh growth of hair such as minoxidil (2,4-diamino-6-piperidinopyrimidine-3-oxide) and its derivatives, diazoxide and phenytoin; other steroidal or nonsteroidal anti-inflammatory agents; carotenoids and especially β-carotene; antipsoriatic agents such as anthralin and its derivatives; inhibitors of $A_2$ phospholipases; antifungus agents, such as imidazoles, triazoles, allylamines or thiocarbamates.

The compositions in accordance with the present invention can also contain flavor improvers, preserving agents, stabilizers, moisture regulators, pH regulators, osmotic pressure modifiers, emulsifiers, UV-A and UV-B sunscreens, antioxidants such as α-tocopherol, butylhydroxyanisole or butylhydroxytoluene, local anesthetics, buffers, and the like.

The compositions in accordance with the present invention can be packaged in delay or progressive release forms, which are known per se. Finally, they can contain ionic (liposomes) or nonionic microcapsules.

The active substance corresponding to general formula (I), in accordance with the present invention, is present in the pharmaceutical or cosmetic compositions in proportions of between 0.01 and 10% by weight relative to the total weight of the composition, and preferably between 0.1 and 5% by weight.

In the therapeutic application, the treatment is determined by the doctor and can vary according to the patient's age, weight and response, and the severity of the symptoms. The dosage is generally between 0.05 and 500 mg/kg/day and preferably between 0.5 and 100 mg/kg/day. The length of the treatment is variable, depending on the severity of the symptoms, and can range between 1 and 12 weeks, continuously or noncontinuously.

The present invention also relates to the use of the compounds of formula (I) in the preparation of pharmaceutical or veterinary compositions in the treatment or for the prophylaxis of allergic diseases and in the treatment of dermatitis and of inflammatory diseases.

The following examples to illustrate the present invention without, however, being of a limiting nature.

REFERENCE EXAMPLE A

Preparation of 2,5,8-heptadecatriyn-1-ol (3)

In a first stage, propylmagnesium chloride is prepared by adding a solution of 53 g of propyl chloride diluted in 100 cm$^3$ of anhydrous THF (tetrahydrofuran) dropwise to a suspension of 16.43 g of magnesium in 300 cm$^3$ of anhydrous THF which is stirred at ambient temperature under an inert atmosphere. The reaction is completed by heating the reaction mixture to the reflux of THF for three hours after the introduction of propyl chloride is finished.

In a second stage, the dianion of propargyl alcohol is formed by adding 19 g of propargyl alcohol, with stirring, to the above reaction mixture, cooled to 0° C. At the end of the addition, the mixture is stirred for another 1 h 30 min at ambient temperature. 0.5 g of copper cyanide is then added and stirring is continued for another 1 h 30 min, still at ambient temperature. 40.54 g of 1-chloro-2,5-tetradecadiyne are introduced dropwise into the mixture thus obtained, cooled to 0° C. The mixture is left to stand overnight at ambient temperature and it is then heated under reflux for 9 hours. The solvent is then removed by evaporation under vacuum and the residue obtained is extracted with methylene chloride. The organic phase is then washed with water, dried over magnesium sulphate and concentrated under reduced pressure. The solid obtained is dissolved in 350 cm$^3$ of boiling hexane. The expected alcohol crystallizes on cooling. It is filtered off and dried. 25 g of 2,5,8-heptadecatriyn-1-ol are obtained in the form of white crystals whose melting point is 48° C. Its $^1$H NMR spectrum is consistent with the expected structure.

REFERENCE EXAMPLE B

Preparation of 2,5,8,11-heptadecatetrayn-1-ol

As in Example A, the dianion of propargyl alcohol is prepared by exchange with propylmagnesium chloride.

In a first stage, 18 g of magnesium, in 600 cm$^3$ of anhydrous THF, are treated with 72 cm$^3$ of chloropropane. Next, when the magnesium is completely converted, 21.8 cm$^3$ of propargyl alcohol are then added at ambient temperature. After 2 hours' stirring at ambient temperature, 3.5 g of cuprous cyanide are introduced.

The mixture is stirred for another 2 hours at ambient temperature and is then cooled to 0° C., at which temperature one equivalent of 1-bromo-2,5,8-tetradecatriyne, prepared as follows, is added.

12.5 cm$^3$ of phosphorus tribromide, followed by 0.1 cm$^3$ of pyridine, are added to a solution of 50 g of 2,5,8-tetradecatriyn-1-ol in 300 cm$^3$ of anhydrous ether. The mixture thus obtained is heated under reflux for 3 hours. It is then poured, at ambient temperature, into a solution of sodium bicarbonate. The ether phase is separated off, washed with water, dried over magnesium sulphate and then evaporated under reduced pressure. The 1-bromo-2,5,8-tetradecatriyne is dissolved in 30 cm$^3$ of anhydrous THF and is introduced into the reaction mixture containing the dianion of propargyl alcohol.

At the end of the introduction, the mixture is stirred for 2 hours and then left overnight. It is then poured into an iced solution of ammonium chloride, and then extracted twice with ethyl acetate. The combined ethyl acetate phases are washed with water and dried over magnesium sulphate. The solvent is then removed by evaporation under vacuum. The blackish product obtained is extracted five times with 150 cm$^3$ of boiling heptane. 2,5,8,11-heptadecatetrayn-1-ol crystallizes on cooling. 25 g of cream-white crystals are obtained, whose melting point is 54°–56° C.

EXAMPLE OF PREPARATION I

Preparation of 3-thia-5,8,11-eicosatriynoic acid 1-bromo-2,5,8-heptadecatriyne is prepared separately.

A stirred mixture of 15 g of 2,5,8-heptadecatriyn-1-ol (3), 2.2 cm$^3$ of phosphorus tribromide, and 3 drops of pyridine in 150 cm$^3$ of anhydrous ether is heated to boiling for 2 hours under an inert atmosphere. Then, at ambient temperature, the mixture is washed initially with sodium bicarbonate, then with water and is dried over magnesium sulphate. This filtered solution is added directly to a solution of potassium thioglycolate, prepared as follows.

8.9 g of potassium hydroxide are added at ambient temperature, under an inert atmosphere, to 4.7 cm$^3$ of thioglycolic acid dissolved in 150 cm$^3$ of methanol. Stirring is continued for 2 hours at ambient temperature. The ethereal bromide solution, prepared previously, is then added to the dianion of thioglycolic acid thus formed. The bromide displacement reaction is very fast. When the bromide is completely converted, the reaction mixture is poured into acidified water. The ether phase is separated off, washed with water, dried over magnesium sulphate, and the solvent is evaporated off. The crude acid obtained is recrystallized twice from boiling heptane. 9 g of 3-thia-5,8,11-eicosatriynoic acid are obtained in the form of beige crystals melting at 63° C.

The $^1H$ and $^{13}C$ NMR spectra are consistent with the expected structure.

The expected product is analyzed in the form of a hemihydrate.

Elemental analysis: $C_{19}H_{26}O_2S \cdot \frac{1}{2}H_2O$

|  | C | H | O | S |
|---|---|---|---|---|
| Calculated | 69.68 | 8.31 | 12.21 | 9.79 |
| Found | 69.75 | 7.52 | 12.77 | 9.93 |

EXAMPLE OF PREPARATION 2

Preparation of N-ethyl-3-thia-5,8,11-eicosatriynamide a) Preparation of N-ethylthioglycolamide

A mixture of 60 g of ethyl thioglycolate and 150 cm³ of a 33% strength aqueous solution of ethylamine is stirred for 48 hours under an inert atmosphere. The N-ethylthioglycolamide is purified by vacuum distillation. 47 g of a colorless liquid, having a boiling point of 95°–98° C./$1.3 \times 10^2$ Pa, are obtained.

b) Preparation of the sodium thiolate of N-ethylthioglycolamide 2.43 g of N-ethylthioglycolamide in a solution in 30 cm³ of methanol are stirred for one hour with 1.2 g of sodium methanolate at 0° C. under an inert atmosphere.

c) Preparation of 1-bromo-2,5,8-heptadecatriyne

A mixture of 5 g of 2,5,8-heptadecatriyn-1-ol, one drop of pyridine and 2 g of phosphorus tribromide in 20 cm³ of ethyl ether is heated under reflux for 3 hours. The ether phase is then washed initially with sodium bicarbonate and then with water, and then dried over magnesium sulphate.

d) Condensation of N-ethylthioglycolamide with 1-bromo-2,5,8-heptadecatriyne The ether solution of 1-bromo-2,5,8-heptadecatriyne, prepared according to the above operating procedure, is added dropwise under an inert atmosphere to a stirred solution, at 0° C., of sodium thiolate of N-ethylthioglycolamide prepared according to operating procedure b) above. The mixture obtained is stirred for 1 hour after the addition is finished. The solvents are then removed by evaporation under vacuum. The product obtained is dissolved in 100 cm³ of methylene chloride. The organic phase is washed with water, dried over magnesium sulphate, concentrated and then deposited onto a silica gel column. The expected amide is eluted with a mixture of methylene chloride and ethyl acetate (97-3). After evaporation of the eluent, 6 g of product are isolated and are recrystallized from isopropyl ether. 4 g of N-ethyl 3-thia-5,8,11-eicosatriynamide are obtained in the form of beige crystals having a melting point of 59° C.

Elemental analysis: $C_{21}H_{31}NOS$

|  | C | H | N | O | S |
|---|---|---|---|---|---|
| Calculated | 72.99 | 9.04 | 4.05 | 4.63 | 9.29 |
| Found | 73.18 | 9.08 | 3.85 | 4.83 | 9.32 |

EXAMPLE OF PREPARATION 3

Preparation of N-(2-hydroxyethyl)-3-thia-5,8,11-eicosatriynamide a) Preparation of N-(2-hydroxyethyl)thioglycolamide

A mixture of 13 g of ethyl thioglycolate and 17 g of ethanolamine, stirred under an inert atmosphere, is heated for 1 hour to a temperature of 70°–80° C., and then for half an hour at 130° C.

The N-(2-hydroxyethyl)thioglycolamide is purified by distillation. B.p.=152° C./5.3 Pa.

b) Preparation of the sodium thiolate of (2-hydroxyethyl)thioglycolamide 0.54 g of sodium methanolate dissolved in 15 cm³ of methanol is added to a solution of 1.35 g of N-(2-hydroxyethyl) thioglycolamide in 15 cm³ of methanol, at 0° C.

Stirring is continued for 1 hour before the introduction of the bromo derivative.

c) Preparation of 1-bromo-2,5,8-heptadecatriyne

This bromide is prepared as in Example 2c) from 2.44 g of 2,5,8-heptadecatriyn-1-ol, which is treated with 1 g of phosphorus tribromide in 15 cm³ of ethyl ether.

d)

The ether solution of 1-bromo-2,5,8-heptadecatriyne is added to the methanolic solution of sodium thiolate of N-(2-hydroxyethyl) thioglycolamide. When the reaction is finished, the mixture of solvents is removed by evaporation under vacuum. The product is dissolved in 50 cm³ of methylene chloride.

The organic phase is washed with water, separated off, dried over magnesium sulphate, concentrated and deposited onto a silica gel chromatography column. The impurities are removed by using methylene chloride as an eluent and the amide is then entrained with ethyl acetate. After evaporation of the eluent, the crystals obtained are washed with pentane. 1.5 g of N-(2-hydroxyethyl)-3-thia-5,8,11-eicosatriynamide, whose melting point is 77° C., are thus isolated. The IR and $^1H$ NMR spectra are consistent with the expected structure.

The elemental analysis corresponds to a partially hydrated product: $C_{21}H_{31}NO_2S \cdot \frac{1}{4}H_2O$

|  | C | H | N | O | S |
|---|---|---|---|---|---|
| Calculated | 68.90 | 8.67 | 3.82 | 9.83 | 8.75 |
| Found | 68.78 | 8.75 | 3.85 | 10.25 | 8.75 |

EXAMPLE OF PREPARATION 4

Preparation of N-ethyl-3-oxo-3-thia-5,8,11-eicosatriynamide

A solution of 0.53 g of 90% strength meta-chloroperbenzoic acid in 10 cm³ of methylene chloride is added dropwise to a solution of 1 g of N-ethyl-3-thia-5,8,11-eicosatriynamide in 15 cm³ of methylene chloride, stirred at 0° C.

One hour later, the reaction mixture is washed with sodium bicarbonate and then with water. The organic phase is dried over sodium sulphate and deposited onto a silica gel column.

The expected sulphoxide is eluted with a mixture of methylene chloride and ethyl acetate (80-20). After evaporation of the eluent, 0.8 g of product is isolated and is recrystallized from 100 cm³ of isopropyl ether.

0.5 g of N-ethyl-3-oxo-3-thia-5,8,11-eicosatriynamide is obtained in the form of white crystals having a melting point of 77° C.

EXAMPLE OF PREPARATION 5

Preparation of N-ethyl-3,3-dioxo-3-thia-5,8,11-eicosatriynamide

A solution of 20 cm³ of methylene chloride, containing equivalents of meta-chloroperbenzoic acid, is added to a solution of 1 g of N-ethyl-3-thia-5,8,11-eicosatriynamide in 20 cm³ of methylene chloride, stirred at 0° C. After this introduction, the reaction mixture is stirred for 2 hours at ambient temperature and is then washed with an aqueous solution of sodium bicarbonate and finally with water.

After removal of methylene chloride by evaporation under vacuum, the expected sulphone is recrystallized from isopropyl ether in the presence of a trace of ethyl acetate. 0.75 g of N-ethyl-3,3-dioxo-3-thia-5,8,11-eicosatriynamide is obtained in the form of beige crystals whose melting point is 83° C. The infrared and $^1$H NMR spectra are consistent with the expected structure.

The product is analyzed in the form of a hemihydrate.
Elemental analysis: $C_{21}H_{31}NO_3S \cdot \frac{1}{2}H_2O$

|  | C | H | N | O | S |
|---|---|---|---|---|---|
| Calculated | 65.25 | 8.34 | 3.62 | 14.48 | 8.29 |
| Found | 65.00 | 7.95 | 3.60 | 14.45 | 8.23 |

EXAMPLE OF PREPARATION 6

Preparation of 3,3-dioxo-3-thia-5,8,11-eicosatriynoic acid 6 cm³ of 110-volume hydrogen peroxide are added to a solution of 6 g of 3-thia-5,8,11-eicosatriynoic acid in 50 cm³ of methylene chloride and 5 cm³ of formic acid, stirred at 0° C.

The mixture is left at ambient temperature for 48 hours and then concentrated to approximately 25 cm³ and cooled to 0° C.

The expected product crystallizes. It is filtered off, washed with dichloromethane, dried and then recrystallized from formic acid. 4.5 g of 3,3-dioxo-3-thia-5,8,11-eicosatriynoic acid are obtained in the form of white crystals whose melting point is 132° C.

Elemental analysis: $C_{19}H_{26}O_4S$

|  | C | H | O | S |
|---|---|---|---|---|
| Calculated | 65.11 | 7.47 | 18.25 | 9.14 |
| Found | 64.82 | 7.10 | 17.93 | 8.86 |

EXAMPLE OF PREPARATION 7

Preparation of methyl 3,3-dioxo-3-thia-5,8,11-eicosatriynoate

A solution of 1 g of 3,3-dioxo-3-thia-5,8,11-eicosatriynoic acid in 50 cm³ of methanol is heated under reflux in the presence of a sulfuric acid catalyst for 48 hours. The mixture is then filtered at ambient temperature. The methanol is evaporated off under reduced pressure.

The expected product recrystallizes from isopropyl ether.

0.75 g of methyl 3,3-dioxo-3-thia-5,8,11-eicosatriynoate is obtained in the form of pearly flakes whose melting point is 69° C.

EXAMPLE OF PREPARATION 8

Preparation of N[(2-hydroxyethyl)oxyethyl]-3-thia-5,8,11-eicosatriynamide 3 g of carbonyldiimidazole are added to a solution of 3.18 g of 3-thia-5,8,11-eicosatriynoic acid in 50 cm³ of 1,2-dichloroethane, stirred at ambient temperature under an inert atmosphere. The mixture thus obtained is heated to a temperature of between 40° and 50° C. for 3 hours. The solution is then cooled to about 10° C. and 2.10 g of diglycolamine are added. 2 hours after the end of the introduction, the reaction mixture is poured into a saturated solution of ammonium chloride. The organic phase is separated off, washed with water, then dried over magnesium sulphate and finally treated with animal charcoal. The solvent is removed by evaporation under vacuum. The product obtained crystallizes on cooling. It is recrystallized from isopropyl ether. 3 g of N—2)-hydroxyethyl) oxyethyl]-3-thia-5,8,11-eicosatriynamide are thus isolated in the form of cream-white crystals having a melting point of 56° C.

Elemental analysis: $C_{23}H_{35}NO_3S$

|  | C | H | N | O | S |
|---|---|---|---|---|---|
| Calculated | 68.11 | 8.70 | 3.45 | 11.83 | 7.91 |
| Found | 68.06 | 8.68 | 3.46 | 12.01 | 7.88 |

EXAMPLE OF PREPARATION 9

Preparation of 3-thia-5,8,11,14-eicosatetraynoic acid 1-bromo-2,5,8,11-heptadecatetrayne and the dianion of thioglycolic acid are prepared separately.

1-bromo-2,5,8,11-heptadecatetrayne.

A mixture of 5 g of 2,5,8,11-heptadecatetrayn-1-ol, 1.25 cm³ of phosphorus tribromide and one drop of pyridine in 15 cm³ of anhydrous ether, stirred in the absence of light, is heated under reflux for 2 hours. The solution is then poured into 100 cm³ of ice water and extracted twice with ethyl ether. The ether phases are washed initially with a solution of sodium bicarbonate and then with water, and finally dried over sodium sulphate.

Dianion of thioglycolic acid.

2.6 g of sodium methylate are added to a solution of 1.6 cm³ of thioglycolic acid in 50 cm³ of methanol, stirred under an inert atmosphere and cooled to 0° C. Stirring is then continued for 2 hours at ambient temperature.

The ether solution containing 1-bromo-2,5,8,11-heptadecatetrayne is added to this solution which is cooled again to 0° C. Half an hour later, the reaction is finished. The reaction mixture is poured into 200 cm³ of a 1N sulfuric acid solution. The ether phase is separated off, washed with water and dried over sodium sulphate. The solvent is evaporated off under reduced pressure. The product obtained is stirred in heptane. The crystals are filtered off and dried. The 4.2 g of 3-thia-5,8,11,14-eicosatetraynoic acid are recrystallized from isopropyl ether.

3 g of cream-white crystals whose melting point is 70° C. are obtained.

Elemental analysis: $C_{19}H_{22}O_2S$

|  | C | H | O | S |
|---|---|---|---|---|
| Calculated | 72.57 | 7.05 | 10.18 | 10.20 |
| Found | 72.50 | 6.97 | 10.26 | 10.12 |

EXAMPLE OF PREPARATION 10

Preparation of
N-[(2-hydroxyethyl)oxyethyl]-3-thia-5,8,11,14-
eicosatetraynamide 0.53 g of carbonyldiimidazole is added, in the absence of light and under an inert atmosphere, to a solution of 0.5 g of 3-thia-5,8,11,14-eicosatetraynoic acid in 20 cm$^3$ of anhydrous dimethylformamide. The mixture is heated to a temperature of 50° C. for 2 hours.

0.33 g of diglycolamine is then added at ambient temperature and the reaction mixture is left overnight. The next day it is poured into 100 cm$^3$ of acidified (1N HCl) ice water, and is extracted three times with 50-cm$^3$ portions of methylene chloride. The organic phases are combined and dried over sodium sulphate and the solvent is removed under reduced pressure. The expected amide is recrystallized from 60 cm$^3$ of isopropyl ether.

0.5 g of N-[(2-hydroxyethyl)oxyethyl]-3-thia-5,8,11,14-eicosatetraynamide is obtained in the form of white crystals having a melting point of 57°-58° C. This amide is analyzed in hydrated form.

Elemental analysis: $C_{23}H_{31}NO_3S.\frac{1}{4}H_2O$

|  | C | H | N | O | S |
|---|---|---|---|---|---|
| Calculated | 68.04 | 7.80 | 3.45 | 12.80 | 7.90 |
| Found | 68.02 | 7.85 | 3.47 | 12.60 | 7.84 |

EXAMPLE OF PREPARATION 11

Preparation of 3-oxo-3-thia-5,8,11,14-eicosatetraynoic acid 10 cm$^3$ of water containing 1 equivalent of sodium bromite are added with stirring, in the absence of light and under an inert atmosphere, to a solution of 0.5 g of 3-thia-5,8,11,14-eicosatetraynoic acid in 10 cm$^3$ of dioxane, stirred at 10° C. After 2 hours the sulphoxide precipitates. It is filtered off, dried under reduced pressure and then recrystallized from isopropyl ether.

300 mg of 3-oxo-3-thia-5,8,11,14-eicosatetraynoic acid are obtained in the form of beige-white crystals having a melting point of 92° C., and analyzed in hydrate form.

Elemental analysis: $C_{19}H_{22}O_3S.\frac{1}{4}H_2O$

|  | C | H | O | S |
|---|---|---|---|---|
| Calculated | 68.12 | 6.78 | 15.52 | 9.57 |
| Found | 68.18 | 6.69 | 15.55 | 9.65 |

EXAMPLE OF PREPARATION 12

Preparation of
3,3-dioxo-3-thia-5,8,11,14-eicosatetraynoic acid 1.05 cm$^3$ of 9.8N hydrogen peroxide are added dropwise to a solution of 1 g of 3-thia-5,8,11,14-eicosatetraynoic acid in a mixture of 10 cm$^3$ of methylene chloride and 1 cm$^3$ of formic acid, stirred in the absence of light and under an inert atmosphere. Stirring is continued for 2 hours and the mixture is then left overnight at ambient temperature. The next day the precipitate formed is filtered off and dried under reduced pressure.

0.7 g of 3,3-dioxo-3-thia-5,8,11,14-eicosatetraynoic acid is obtained in the form of white crystals having a melting point of 142° C. This product is analyzed in hydrate form.

Elemental analysis: $C_{19}H_{22}O_4S.\frac{1}{2}H_2O$

|  | C | H | S |
|---|---|---|---|
| Calculated | 65.20 | 6.52 | 9.02 |
| Found | 64.44 | 6.42 | 8.96 |

The following examples illustrate pharmaceutical and/or cosmetic compositions in accordance with the present invention.

EXAMPLE 1

The following composition is prepared:

| N-[(2-hydroxyethyl)oxyethyl]-3-thia-5,8,11-eicosatriynamide | 0.50 g |
|---|---|
| 1-Propanol | 50.00 g |
| Propylene glycol | 10.00 g |
| Hydroxypropyl cellulose | 2.00 g |
| Water | q.s. 100.00 g |

This composition is in the form of a gel which can be applied topically.

EXAMPLE 2

The following composition is prepared:

| N-(2-hydroxyethyl)-3-thia-5,8,11-eicosatriynamide | 5.00 g |
|---|---|
| Micronized polyethylene | 10.00 g |
| Isopropyl myristate | q.s. 100.00 g |

This composition is in the form of a hydrophobic ointment for topical application. Good results are also obtained by replacing N-(2-hydroxyethyl)-3-thia-5,8,11-eicosatriynamide with N-ethyl-3,3-dioxo-3-thia-5,8,11-eicosatriynamide.

EXAMPLE 3

The following composition is prepared:

| N-ethyl-3,3-dioxo-3-thia-5,8,11-eicosatriynamide | 1.00 g |
|---|---|
| Triglycerides of capric, caprylic and stearic acids | 40.00 g |
| Triglycerides of capric and caprylic acids | 30.00 g |
| Petrolatum | 20.00 g |
| Petrolatum oil | q.s. 100.00 g |

This composition is in the form of a hydrophobic ointment for topical application.

EXAMPLE 4

The following composition is prepared:

| 3,3-dioxo-3-thia-5,8,11-eicosatriynoic acid | 0.50 g |
|---|---|
| Cetyl alcohol | 6.40 g |
| Cetyl alcohol oxyethylenated with 20 | 2.10 g |

-continued

| moles of ethylene oxide | |
|---|---|
| Glycerol monostearate | 2.00 g |
| Triglycerides of capric and caprylic acid | 15.00 g |
| Propylene glycol | 10.00 g |
| Water | q.s. 100.00 g |

This composition is in the form of a cream for topical application.

EXAMPLE 5

The following lotion is prepared:

| 3,3-dioxo-3-thia-5,8,11-eicosatriynoic acid | 0.10 g |
|---|---|
| Ethanol | 50.00 g |
| Propylene glycol | q.s. 100.00 g |

The compositions of preceding Examples 1 to 5 are all manufactured and stored in an inert atmosphere and in the absence of light.

EXAMPLE 6

The following composition is prepared:

| N-(2-hydroxyethyl)-3-thia-5,8,11-eicosatriynamide | 0.10 g |
|---|---|
| Absolute ethanol | 1.00 cm³ |
| Flavoring q.s., preserving agent q.s. | |
| Glycerol | q.s. 5.00 cm³ |

This composition is introduced into a 5-cm³ brown glass ampoule to be employed orally in the form of a drinkable solution.

EXAMPLE 7

A 350-mg gelatin capsule containing a powder having the following composition is prepared:

| N-[(2-hydroxyethyl)oxyethyl]-3-thia-5,8,11,14-eicosatetraynamide | 0.025 g |
|---|---|
| Microcrystalline cellulose | 0.020 g |
| Corn starch | 0.100 g |
| Colloidal silica | 0.020 g |
| Magnesium stearate | 0.185 g |

EXAMPLE 8

A gel is prepared in the form of a microcapsular dispersion having the following formulation:

| 3-thia-5,8,11-eicosatriynoic acid | 0.10 g |
|---|---|
| Phosphatidylcholine | 5.00 g |
| Butylhydroxytoluene | 0.10 g |
| Crosslinked polyacrylic acid, sold under the name of Carbopol 940 by Goodrich | 0.50 g |
| Methyl para-hydroxybenzoate | 0.01 g |
| Dilute HCl or NaOH q.s. | pH = 7.4 |
| 0.9% NaCl | q.s. 100.00 g |

The preparation process comprises the following stages:

1) The methyl para-hydroxybenzoate is dissolved in a 0.9% NaCl solution.

2) The butylhydroxytoluene is dissolved in a few ml of $CHCl_3$, the phosphatidylcholine is added to it, and the quantity is made up to 60 ml with $CHCl_3$. The whole is stirred magnetically until dissolved. The 3-thia-5,8,11-eicosatriynoic acid is added and stirring is continued again until dissolution.

$CHCl_3$ is then evaporated off, the lipid phase being taken to dryness in a rotary evaporator.

3) The solution obtained during the first stage is added, with suitable mechanical stirring (3 hours at 200 rpm and at 20° C.) to the lipid phase obtained in the second stage. This produces a homogeneous milky dispersion of microcapsules which have a diameter of 0.5 μm to 5 μm.

4) Carbopol 940 is sprinkled, with stirring, into the dispersion thus obtained and the pH of the gel is adjusted to 7.4 with dilute sodium hydroxide.

What is claimed is:

1. A compound having the formula $$C_5H_{11}-A-CH_2-C\equiv C-CH_2-C\equiv C-$$
$$-CH_2-C\equiv C-CH_2-S-CH_2-COR$$
$$\downarrow$$
$$(O)_n$$

wherein
A represents $-(CH_2)_2-$ or $-(C\equiv C)-$,
n is equal to 0, 1 or 2,
R represents hydroxyl or alkoxy having the formula $OR_1$ and
$R_1$ represents alkyl containing 1-20 carbon atoms, monohydroxyalkyl, polyhydroxyalkyl, aryl or aralkyl,
and the salt of said compound and its optical and geometric isomers.

2. The compound of claim 1 wherein said alkyl represents a member selected from the group consisting of methyl, ethyl, isopropyl, butyl, tert. butyl, 2-ethylhexyl, isooctyl, dodecyl, hexadecyl and octadecyl.

3. The compound of claim 1 wherein said polyhydroxyalkyl contains 3-6 carbon atoms and 2-5 hydroxyl groups.

4. The compound of claim 1 wherein said aryl is phenyl or phenyl substituted by at least one of halogen, —OH, —NO₂, lower alkyl, trifluoromethyl and carboxylic acid functional group.

5. The compound of claim 1 wherein said aralkyl is benzyl or phenethyl.

6. A compound having the formula $$C_5H_{11}-A-CH_2-C\equiv C-CH_2-C\equiv C-CH_2-C\equiv C-CH_2-S-CH_2-COR$$
$$\downarrow$$
$$(O)_n$$

wherein
A represents $-(CH_2)_2-$ or $-(C\equiv C)-$,
n is equal to 0, 1 or 2,
R represents hydroxyl, and the salt of said compound and its optical and geometric isomers.

7. The compound of claim 6 wherein said salt is a salt of an alkali metal, an alkaline earth metal, zinc or an organic amine.

8. The compound of claim 6 selected from the group consisting of 3-thia-5,8,11-eicosatriynoic acid,
3-thia-5,8,11-eicosatetraynoic acid,
3-oxo-3-thia-5,8,11-eicosatriynoic acid,
3-oxo-3-thia-5,8,11,14-eicosatetraynoic acid,
3,3-dioxo-3-thia-5,8,11-eicosatriynoic acid and
3,3-dioxo-3-thia-5,8,11,14-eicosatetraynoic acid.

9. A method for the treatment inflammatory diseases, an effective amount of the compound of claim 6.

10. The method of claim 9 wherein said compound is administered in a dosage ranging from 0.05 to 500 mg/kg/day.

11. The method of claim 9 wherein said compound is administered in a dosage ranging from 0.5 to 100 mg/kg/day.

12. A compound having the formula

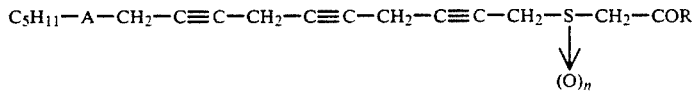

wherein
A represents $-(CH_2)_{\overline{2}}$ or $-(C\equiv C)-$,
n is equal to 0, 1 or 2,
R represents hydroxyl, or alkoxy having the formula $-OR_1$ wherein $R_1$ represents alkyl containing 1-20 carbon atoms, monohydroxyalkyl or polyhydroxyalkyl,
and the salt of said compound and its optical and geometric isomers.

* * * * *